(12) United States Patent
Golz et al.

(10) Patent No.: US 11,953,667 B2
(45) Date of Patent: Apr. 9, 2024

(54) DEVICE FOR ACTUATOR-DRIVEN ADJUSTMENT OF THE MAGNIFICATION STAGES OF A MAGNIFICATION SELECTOR

(71) Applicant: Carl Zeiss Meditec AG, Jena (DE)

(72) Inventors: David Golz, Jena (DE); Dietrich Martin, Jena (DE); Ingo Koschmieder, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 788 days.

(21) Appl. No.: 16/638,571

(22) PCT Filed: Aug. 23, 2018

(86) PCT No.: PCT/EP2018/072787
§ 371 (c)(1),
(2) Date: Feb. 12, 2020

(87) PCT Pub. No.: WO2019/038386
PCT Pub. Date: Feb. 28, 2019

(65) Prior Publication Data
US 2020/0218049 A1 Jul. 9, 2020

(30) Foreign Application Priority Data
Aug. 24, 2017 (DE) .................... 10 2017 214 790.3

(51) Int. Cl.
*G02B 21/00* (2006.01)
*G02B 21/02* (2006.01)
(Continued)

(52) U.S. Cl.
CPC .......... *G02B 21/025* (2013.01); *G02B 23/00* (2013.01); *A61B 3/135* (2013.01); *A61B 90/20* (2016.02); *G02B 21/0012* (2013.01)

(58) Field of Classification Search
CPC ...... G02B 21/00; G02B 21/02; G02B 21/025; G02B 21/361; G02B 25/002; G02B 25/005; G02B 23/00
(Continued)

(56) References Cited

U.S. PATENT DOCUMENTS 3,652,153 A * 3/1972 Gambs ................... A61B 3/135
351/205
5,995,282 A * 11/1999 Akiyama ........... G02B 21/0012
359/368
(Continued)

FOREIGN PATENT DOCUMENTS

DE        103 24 238 A1    12/2004
DE    10 2006 058943 A1     6/2008
(Continued)

OTHER PUBLICATIONS

International Search Report for PCT/EP2018/072787, dated Nov. 8, 2018, 3 pages.
(Continued)

*Primary Examiner* — Thong Q Nguyen
(74) *Attorney, Agent, or Firm* — De Witt LLP (57) ABSTRACT

A device by which the magnification stages of a magnification selector based on Galilean telescope systems can be adjusted by a motor. The magnification selector has a sensor that transmits the currently magnification stage to a control unit; in the control unit, an assignment of the magnification stages present on the magnification selector to a sequence of the magnification stages, organized based on size, is stored. For the user, there are operating elements connected to the control unit for selecting a magnification stage. In order to set the magnification stage selected by the user via the operating elements, the magnification selector has an actuator, which is connected to the control unit to receive appropriate control signals. Although provided in particular for
(Continued)

slit lamps and surgical microscopes having eyepieces, the solution can also be applied in other ophthalmological devices or devices from other technical fields.

23 Claims, 5 Drawing Sheets (51) Int. Cl.
*G02B 23/00* (2006.01)
*A61B 3/135* (2006.01)
*A61B 90/20* (2016.01)

(58) Field of Classification Search
USPC ......... 359/432, 676, 368–398, 399, 421–422
See application file for complete search history.

(56) References Cited

U.S. PATENT DOCUMENTS

| 7,380,943 | B2* | 6/2008 | Koschmieder | A61B 3/135 |
| | | | | 351/246 |
| 7,411,739 | B2* | 8/2008 | Obrebski | G02B 26/005 |
| | | | | 349/200 |
| 7,808,541 | B2* | 10/2010 | Shikano | H04N 5/232939 |
| | | | | 348/333.12 |
| 2007/0019288 | A1* | 1/2007 | Karasawa | G02B 21/025 |
| | | | | 359/380 |
| 2016/0241773 | A1 | 8/2016 | Shida et al. | |

FOREIGN PATENT DOCUMENTS

| DE | 10 2008 045 826 A1 | 3/2010 |
| DE | 10 2010 018 500 A1 | 10/2011 |
| EP | 2 950 130 A1 | 12/2015 |
| JP | 2014-38359 | * 2/2014 |

OTHER PUBLICATIONS

English translation of International Search Report for PCT/EP2018/072787, dated Nov. 8, 2018, 2 pages.

Jean-Marie A. Parel u. a .; "Remote Controlled Stereo Slit-Lamp for Imaging Inaccessible Patients"; ARVO Annual Meeting; IOVS Mar. 2012, vol. 53, 3633.

Jean-Marie A: Parel u. a .; "Second Generation Robotic Remote Controlled Stereo Slit-Lamp"; ARVO Annual Meeting; IOVS Sep. 2016, vol. 57, 1721.

Tanabe.N. [et al.]: A Remote Operating SLit Lamp Microscope System. In: Methods Inf Med, vol. 50, 2011, S. 427-434.

Search Report for DE 10 2017 214 790.3, dated Aug. 24, 2017, 12 pages.

* cited by examiner

FIG. 1

PRIOR ART

PRIOR ART

DEVICE FOR ACTUATOR-DRIVEN ADJUSTMENT OF THE MAGNIFICATION STAGES OF A MAGNIFICATION SELECTOR

RELATED APPLICATIONS

This application is a National Phase entry of PCT Application No. PCT/EP2018/02787 filed Aug. 23, 2018, which application claims the benefit of priority to DE Application No. 10 2017 214 790.3, filed Aug. 24, 2017, the entire disclosures of which are incorporated herein by reference.

TECHNICAL FIELD OF THE INVENTION

The present invention relates to a device with which the magnification levels, in particular of a magnification changer based on Galilean telescope systems, can be adjusted by means of an actuator.

BACKGROUND

Numerous technical solutions for this purpose are known from the prior art.

For example, the component that realizes the change in magnification on slit lamps and surgical microscopes is for example arranged in a collimated region of the beam path. This component usually consists of a cylindrical element with three or more passages, which are brought into the beam path by rotating. As a rule, the cylindrical element has a free, direction-independent passage, which corresponds to the magnification factor 1.

In the other available passages, at least two optical elements are arranged in each case such that they form a Galilean telescope. In the case of a Galilean telescope, the beam path is used depending on the direction either for a (parallel) expansion or (parallel) reduction in the cross section of the beam, which is equivalent to a magnification or reduction in size of the image. The passages with Galilean telescope systems are thus direction-dependent and each provide two magnification levels.

A disadvantage here, however, is that with a 5-way changer it is not possible to achieve an ascending or descending sequence of magnifications by continuously rotating (in one direction). For continuously increasing or decreasing magnification levels, a double step and then a reversal of the direction of rotation are required in the case of at least one change.

Figure 1:
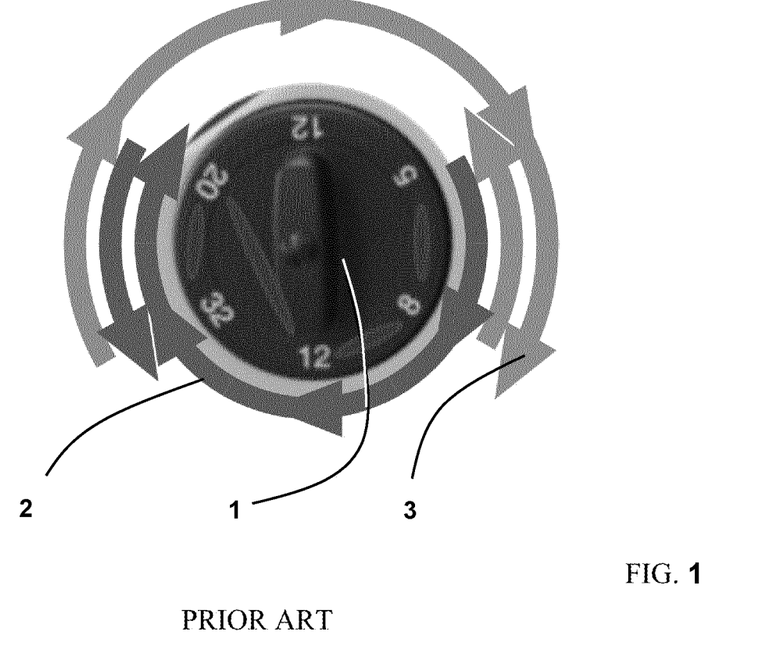
FIG. 1 depicts a rotary magnification changing selector according to the prior art.

For this purpose, FIG. 1 shows the schematic representation of the operating button 1 of a magnification changer of a slit lamp. The numerical values present on the operating button 1 are only intended to illustrate increasing or decreasing magnification levels and do not correspond to the actual, optical magnification values. It is evident from FIG. 1 that the operating button 1 should be turned incrementally to the left to incrementally increase of the magnification from 5 to 8 and further to 12. From level 12 to level 20, a double step is then required and from level 20 to level 32 a step with direction reversal (i.e., to the right) is required, in order to reach the corresponding magnification with the fewest switching processes. This is to be expressed by the dark gray arrows 2.

For an incremental reduction of the magnification, a double step and a direction reversal are likewise required, however, between other magnification levels, which is expressed by the light gray arrows 3. This leads to the situation that most operators do not (can not) know how to move the magnification changer to enlarge the field of view or to increase the resolution.

Especially for magnification changers on slit lamps and surgical microscopes with eyepieces, this means that the operators simply carry out trial and error and sometimes even achieve the desired change immediately. Or else, the operators look at the magnification changer in order to bring it into the correct position.

Both approaches are not very intuitive and interrupt the examination process considerably. As a result of the operator moving away from the eyepieces and turning his gaze to the magnification changer, he is forced to refocus his eyes. Sometimes he even has to put on reading glasses for this.

In addition, he also loses control over the patient in the process and the risk increases that he loses from his field of view a detail that interests him in the eye to be examined and after the magnification change, he must laboriously search and find it again.

Other technical solutions are known from the prior art, in which the magnification levels of a magnification changer are adjusted by motor.

The Association for Research in Vision and Ophthalmology (ARVO) is the largest gathering of eye and vision researchers in the world and attracts over 11 000 participants from more than 75 countries every year.

At their annual conferences, trends and new developments in ophthalmology, such as for example also in relation to slit lamps, are reported on.

Jean-Marie A. Parel et al. introduced a remote-controlled stereo slit lamp for patients in inaccessible areas in 2012 [1]. To this end, a slit lamp from Carl Zeiss Meditec AG was modified to implement a motorized movement mechanism. Furthermore, the angle of incidence, width, height, intensity and the magnification of the slit were controlled by a computer system. The images or videos captured by a camera could be displayed in real time via an integrated graphical user interface and transmitted via local network, Internet and satellite.

At the annual conference in 2016, Jean-Marie A. Parel et al. reported on the second generation of remote-controlled stereo slit lamps [2]. The main focus on this occasion was on an improved feature set to transmit stereoscopic live views together with bi-directional audio communication in real time via a network or internet connection to special institutes for eye research.

A second-generation remote-controlled stereo slit lamp was successfully tested between two institutes, wherein the slit lamp was used in India, while the images, together with audio communication, were transmitted to the USA.

The successful testing of a second-generation remote-controlled stereo slit lamp shows that it is possible to use this instrument even in rural areas, specifically without the need for a specialist or physician to be present on site.

However, for inexplicable reasons, even in highly modern, remote-controlled slit lamp prototypes, the actual logical sequence for the magnification change is not made available to the user.

Figure 2:
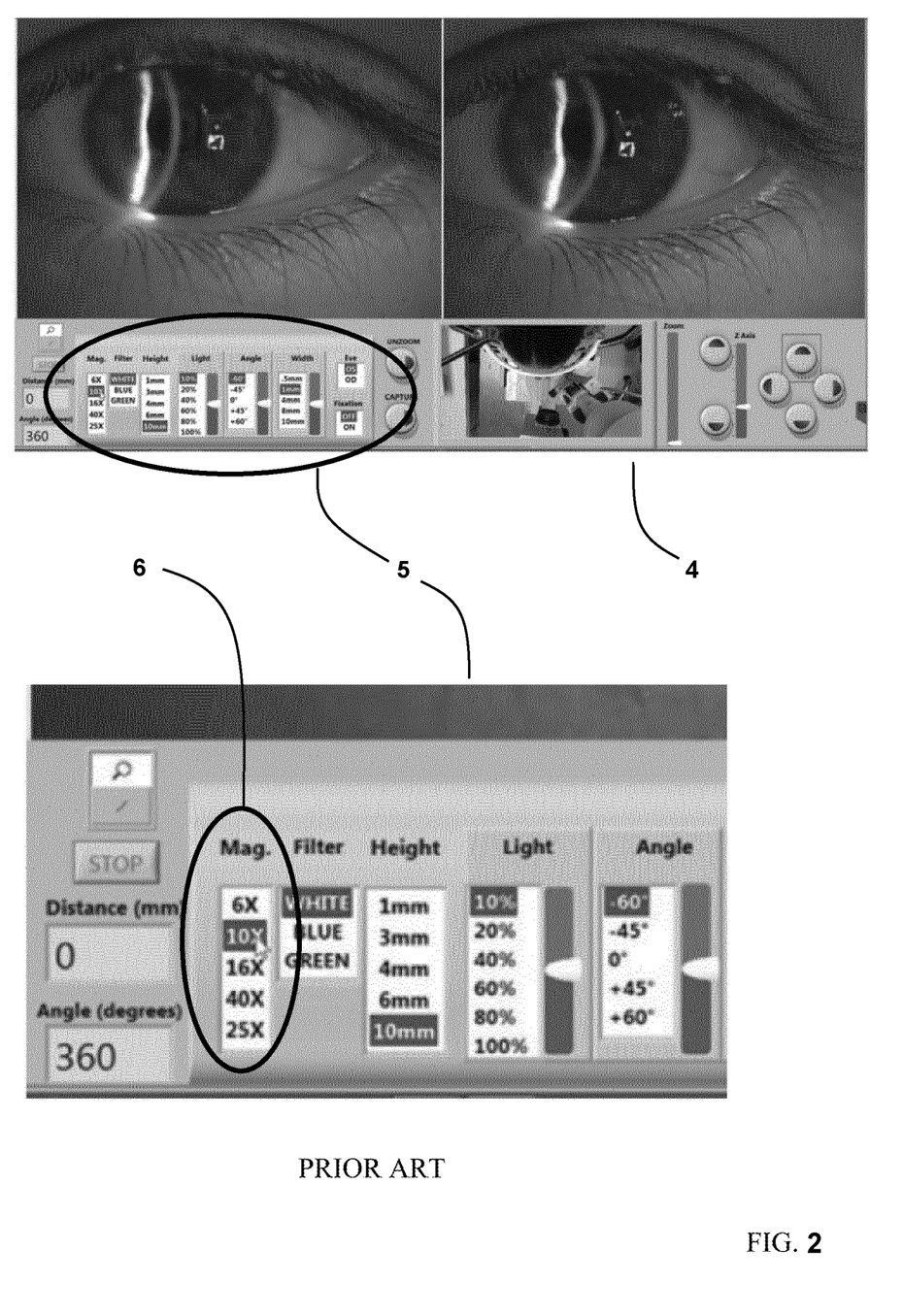
FIG. 2 depicts a graphical user interface for magnification selection according to the prior art.

For this purpose, FIG. 2 shows the operator interface of a remote-controlled slit lamp according to [2]. While the upper image shows the entire operator interface 4, only the setting options for the magnification 5 are listed in the lower image. It is evident that the magnification levels do not form a continuously increasing sequence 6. Thus, the operation in situ is difficult and is connected with the disadvantages already mentioned.

LITERATURE

[1] Jean-Marie A. Parel et al.; "Remote Controlled Stereo Slit-Lamp for Imaging Inaccessible Patients"; ARVO Annual Meeting; lOVS March 2012, Vol. 53, 3633
[2] Jean-Marie A: Parel et al.; "Second Generation Robotic Remote Controlled Stereo Slit-Lamp"; ARVO Annual Meeting; lOVS September 2016, Vol. 57, 1721

SUMMARY OF THE INVENTION

Embodiments of the present invention provide a solution for simplifying the actuator-driven adjustment of the magnification levels of an optical magnification changer. In particular, the magnification change should be as simple and intuitive for the operator as possible. In so doing, the solution should be suitable for slit lamps or surgical microscopes, in particular also those with eyepieces and/or systems based on Galilean telescope systems.

Example embodiments of the invention include a device for actuator-driven adjustment of the magnification levels of a magnification changer, by means of the magnification changer having a sensor for transmitting the currently present magnification level to a control unit, in the control unit being stored an assignment of the magnification levels present on the magnification changer to a sequence of the magnification levels ordered according to size, operating elements for choosing a magnification level being present for the user and being connected to the control unit and the magnification changer for setting the magnification level chosen by the user via the operating elements having an actuator which is connected to the control unit to receive corresponding control signals.

Example embodiments of the invention relate to a device with which the magnification levels can be adjusted using actuators. Although the solution is intended in particular for magnification changers on slit lamps and surgical microscopes with eyepieces, it could in principle also be used in other ophthalmic appliances or also in appliances from other technical fields. In particular, the device is also suitable for magnification changers based on Galilean telescope systems. Accordingly, while discussed in the context of slit lamps and surgical microscopes, the invention should not be considered limited to these applications.

DETAILED DESCRIPTION

The invention is described in more detail below on the basis of example embodiments.

Figure 3:
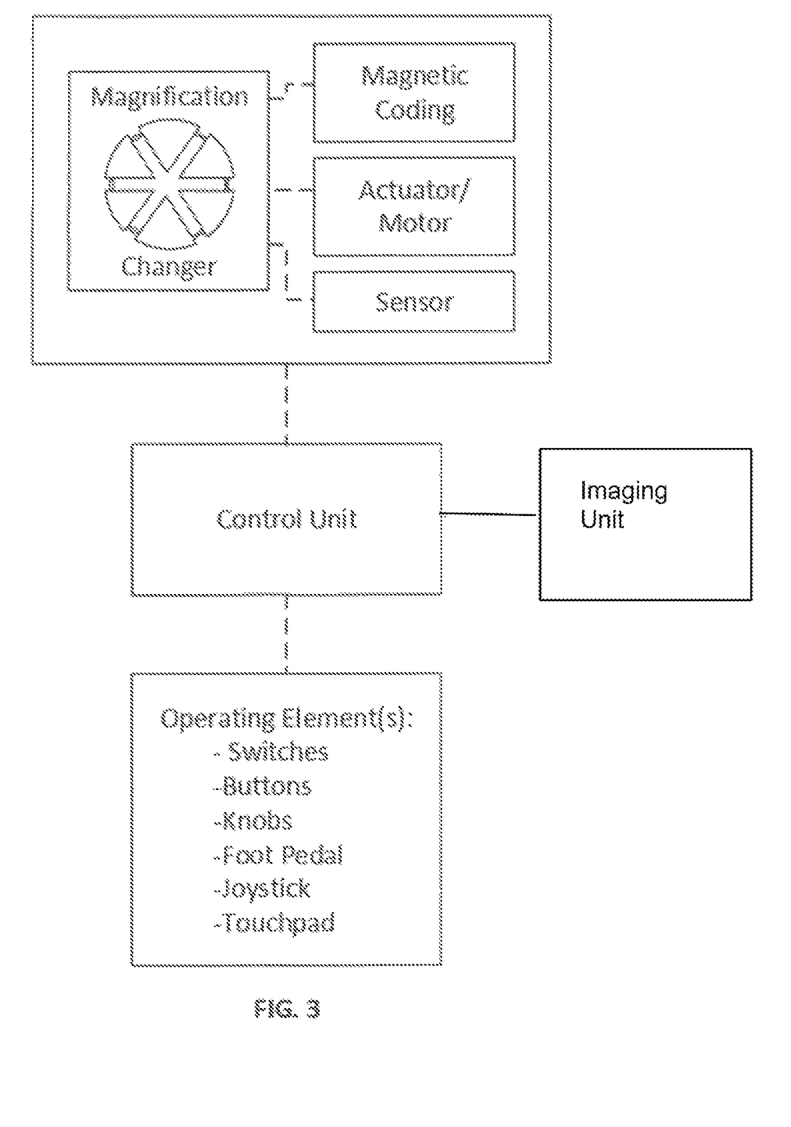
FIG. 3 is a block diagram of a device according to an example embodiment of the invention.

The device according to an example embodiment of the invention is used for actuator-driven adjustment of the magnification levels, in particular of a magnification changer based on Galilean telescope systems.

According to example embodiments of the invention, the magnification changer has a sensor for transmitting the currently present magnification level to a control unit and an actuator for setting the magnification level chosen by the user via the operating elements.

For this it is necessary that the sensor continuously monitors the set magnification and that this is made available to the control unit absolutely (for example) or as a relative value. Here the detection of the absolute position has the advantage that the current position of the magnification changer is immediately known when the entire appliance is switched on. Moreover, when detecting the absolute position, it does not matter which magnification level was previously active and also whether the adjustment was actuator-driven or manual.

When the relative position is detected, an "orientation run" is sometimes required after switching on the entire appliance and, under certain circumstances, from time to time, in which the relative position of the magnification changer to a fixed mark is determined. Then every movement or change in the magnification changer be monitored and transmitted to the control unit.

According to the invention, an assignment of the sensor value to each magnification level together with the sequence of the possible magnification levels is stored in the control unit. This assignment contains the number of switching steps that are required to get to the next larger or smaller magnification state.

The operating elements for choosing a magnification level, which are available to the user, are operably connected to the control unit.

A control signal is transmitted by the control unit to the actuator present at the magnification changer from the currently present magnification level detected by the sensor, the magnification level chosen by the user via the operating elements and the assignment stored in the control unit of the magnification levels present at the magnification changer to a sequence ordered according to size, and so said actuator sets the new magnification level chosen by the user.

For a change in the visual impression, the user only needs to decide whether he requires a larger field of view or a higher magnification (hence a smaller field of view). Accordingly, he actuates the operating element so that the control unit generates a corresponding control signal, transmits said control signal to the actuator of the magnification changer and thus either the next smaller or the next larger magnification level is set depending on the control signal.

According to a first example embodiment, there is in the magnification changer a bijection between magnetic codings and magnification levels present. In this case, the sensor for transmitting the currently present magnification level to the control unit can be one sensor or a plurality of sensors based on the HALL effect. This makes it possible to detect the absolute position with the advantages already mentioned.

In particular with limited installation space, the magnetic coding can be carried out in such a way that the magnets to be detected are e.g. alternately arranged with different pole directions and different installation depths on only one track and the different magnetic flux densities are detected by the Hall sensor.

In the magnetic Hall sensor system, it is also possible to use an arrangement of the magnets based on the GRAY code coding. The latter allows a simple analysis of any error states that may occur when switching.

For absolute coding of the magnification levels, optical (e.g. fork or reflex couplers) or inductive couplers can also be used.

According to a second example embodiment, routines are additionally stored in the control unit, which contain the further procedure after the respective end positions have been reached.

In principle, there is the possibility here that when the largest or smallest magnification level is reached, the magnification changer is not switched onward and the user has to move the operating element in the opposite direction in order to bring about a change. In addition, the system can still provide the user with acoustic or visual feedback that the end has been reached.

A further example embodiment relates to the operating elements for the user. For example, only one operating element or two operating elements or functions for "larger" and "smaller" can be available to the user for choosing a magnification level, or a separate operating element is available to him for each magnification level.

If only one operating element is available to the user for choosing a magnification level, it should be possible, however, for the operating element to be actuated multiple times in order to change the magnification by more than one level. The sensor, control unit and actuator should be able to implement this one after the other immediately.

With the use of separate operating elements for each magnification level, it would be possible for the user to choose the magnification level he wanted directly and not only to adjust it incrementally.

Switches, buttons, knobs, foot pedals or else joysticks and touchpads are used as operating elements.

A further example embodiment relates to the actuator present at the magnification changer. The actuator for the adjustment of the magnification changer is for example an electric motor, which is attached directly or via a gear to its shaft and is designed such that it can (for example) also be moved by hand. However, it is also possible that the actuator is part of the magnification changer as a round linear or traveling wave motor and that a manual adjustment is not possible.

According to another embodiment, the sensor for detecting the absolute position of the magnification changer is integrated in the actuator.

Here, the actuator control can be designed such that the actuator switches off after reaching the chosen magnification level, is supplied with an auxiliary voltage different from the operating voltage or remains at full voltage.

According to another example embodiment the sensor on the magnification changer is designed to also capture movements made by hand and to transmit the currently present magnification level to the control unit.

This has the advantage that even for a manual adjustment of the magnification changer, its absolute position is captured and transmitted to the control unit.

A further example embodiment relates to the control unit, which is designed to use the currently present magnification level, the magnification level chosen by the user via the operating elements and the assignment stored in the control unit to generate appropriate control signals and to transmit them to the actuator.

The control unit is for example furthermore designed to record the implemented magnification change or the end position reached for the user via optical, acoustic or similar signaling.

It is possible to give visual feedback about the currently set magnification on a display element in an ergonomically favorable position for viewing or in the vicinity of the operating element. Furthermore, it is possible to give information about the operating state, such as for example reaching the current end positions, acoustically or haptically. Here, the current magnification level can be shown via an additionally present imaging unit.

Figure 5:
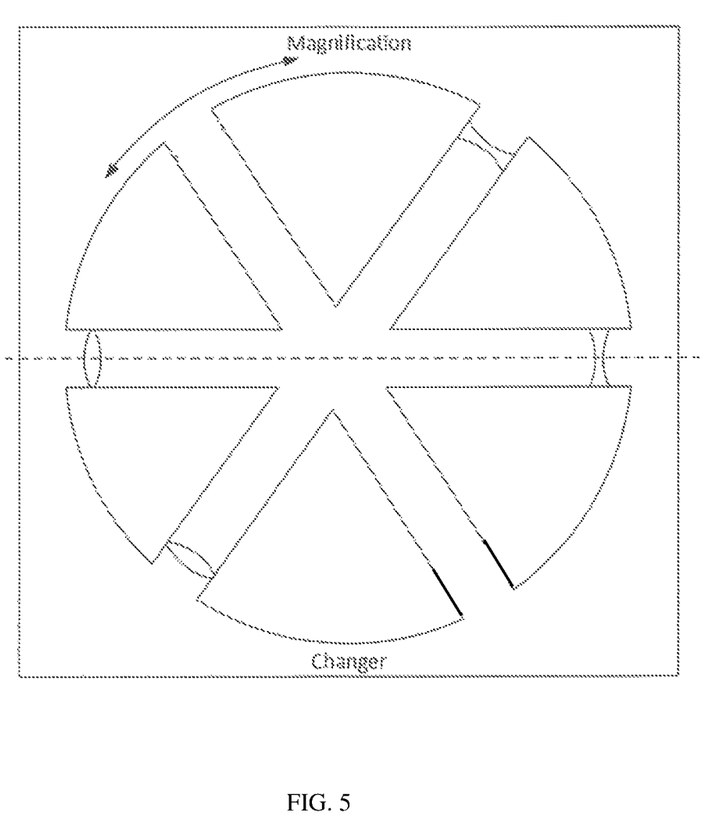
FIG. 5 is a block diagram of a magnification changer according to an example embodiment of the invention with a free passage of the magnification changer depicted.

The magnification changer on which the invention is based has one free passage and two passages each with a Galilean telescope system, which passages are arranged offset by approximately 60° and can be brought into the beam path by a rotational movement; however, said magnification changer can likewise be made with only exactly 2 passages (e.g. 1× free, 1× with optics) or else more than a total of 3 passages.

Figure 4:
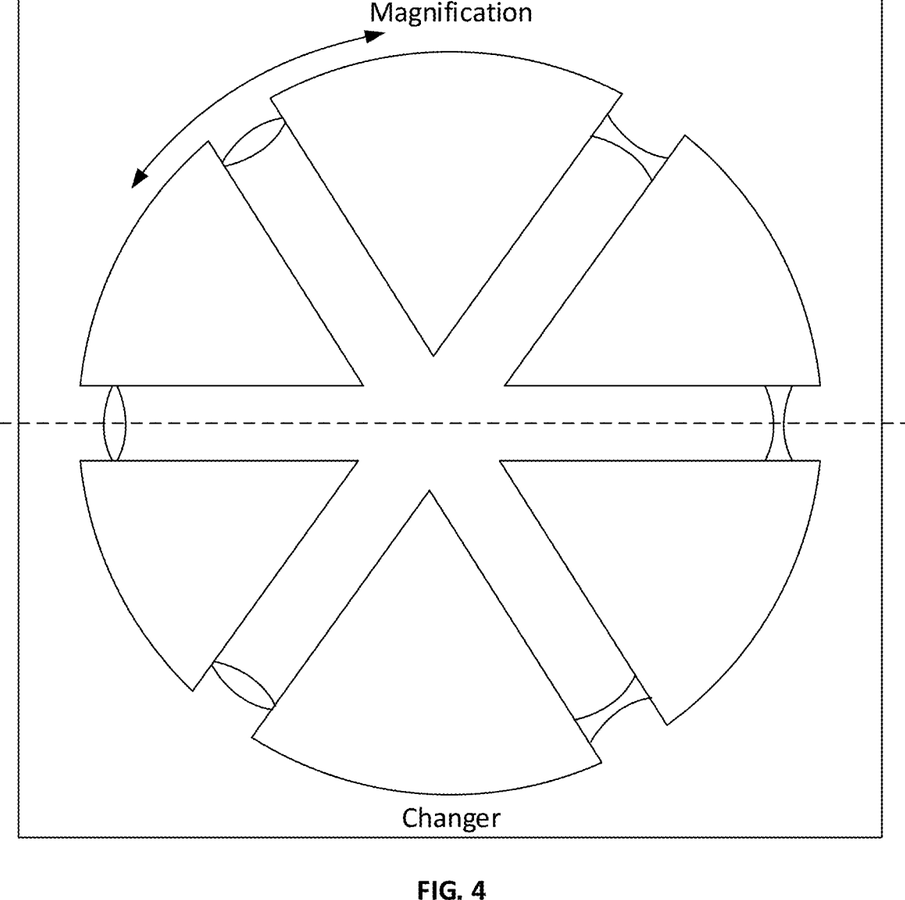
FIG. 4 is a block diagram of a magnification changer according to an example embodiment of the invention with optional optical elements inserted into a free passage of the magnification changer.

The free passage is present twice (forwards and backwards respectively) without offering a use connected therewith. According to a last example embodiment, the magnification changer has one or more optical elements which are optionally insertable into the free passage if the changer is oriented in the one direction or not if the changer is oriented in the other respective direction. As a result, it is possible to make the free passage of the magnification changer optically active in at least one direction. It is therefore possible, e.g. to augment the usual discrete magnification levels of a three-fold or five-fold magnification changer by an additional level. For example for a particularly high magnification or a large field of view. The insertion of the additional optical element or elements is made possible or prevented depending on the direction of the changer. This can be achieved by evaluating the position via the sensors and control unit or else by simple measures using mechanical components that activate and deactivate the optical element when pivoting past, for example via pinions, cams, gravity or spring elements.

The optical element, which is insertable into the free passage of the magnification changer, is in this case e.g. an additional lens, whereby one of the two free passages additionally can be used optically.

With the solution according to the invention a device is made available, with which the magnification levels of a magnification changer based on Galilean telescope systems can be adjusted in actuator-driven fashion. In particular the device is distinguished by the magnification change being simple and intuitive for the operator. In a second independent example embodiment, the range of available magnifications or field of view diameters can be augmented by an additional level by using one of the two free passage directions with a selective optical effect.

Although the solution is intended in particular for magnification changers on slit lamps and surgical microscopes with eyepieces, it can in principle also be used in other ophthalmic appliances or also in appliances from other technical fields.

Benefits of the device can be seen in that the user of slit lamps or surgical microscopes with eyepieces can change the magnification without taking his gaze off the eyepieces and thus the eye to be examined. If he has considered whether he requires a larger field of view or a higher magnification, he actuates the corresponding operating element.

The solution described here can also be applied analogously to systems in which cameras are used instead of the eyepieces and the image is displayed on a monitor.

The invention claimed is:

1. A device for actuator-driven adjustment of incremental magnification levels of a magnification changer, comprising:

at least one sensor coupled to the magnification changer that detects and transmits a currently selected incremental magnification level to a control unit;

the control unit including a stored assignment in memory of the incremental magnification levels that are available to be selected on the magnification changer in a sequence of the incremental magnification levels ordered according to numerical size;

at least one operating element that enables choosing a desired magnification level, wherein the at least one operating element that enables choosing the desired magnification level is presented to a user and is connected to the control unit; and the magnification changer that sets the magnification level chosen by the user via the at least one operating element further comprises an actuator which is connected to and controlled by the control unit and which receives corresponding control signals from the control unit and that is operably mechanically coupled to the magnification changer to change the incremental magnification level thereof.

2. The device as claimed in claim 1, further wherein the at least one sensor is configured to transmit the currently selected magnification level to the control unit and to detect positions of the magnification changer.

3. The device as claimed in claim 1, wherein in the magnification changer there is a bijection between magnetic codings and the incremental magnification levels that are available to be selected and the at least one sensor that transmits the currently selected incremental magnification level to the control unit is based on Hall effect.

4. The device as claimed in claim 1, wherein the assignment stored in the control unit additionally comprises routines to process control signals which are received from the magnification changer that is oriented in end positions.

5. The device as claimed in claim 1, wherein only one operating element is available to the user for choosing the incremental magnification level.

6. The device as claimed in claim 1, wherein exactly two operating elements are available to the user to choose the incremental magnification level.

7. The device as claimed in claim 6, wherein the operating elements available to the user for choosing the incremental magnification level are haptically distinguishable.

8. The device as claimed in claim 1, wherein the at least one operating element available to the user for choosing the incremental magnification level are haptically distinguishable.

9. The device as claimed in claim 1, further comprising a separate operating element for each of the incremental magnification levels that is available to the user for choosing the incremental magnification level.

10. The device as claimed in claim 1, wherein the at least one operating element further comprises components selected from a group consisting of switches, buttons, knobs, foot pedals, joysticks, touchpads and a combination of the foregoing.

11. The device as claimed in claim 1, wherein the actuator for the adjustment of the incremental magnification levels of the magnification changer comprises an electric motor, which is attached directly or via a gear to a shaft of the incremental magnification changer and is designed such that the incremental magnification changer can also be moved by hand.

12. The device as claimed in claim 1, wherein the at least one sensor detects a position of the incremental magnification changer and is integrated in the actuator.

13. The device as claimed in claim 1, wherein the at least one sensor at the magnification changer is configured to also capture movements made by hand and to transmit the currently selected magnification level to the control unit.

14. The device as claimed in claim 1, wherein the control unit is configured to use a currently selected magnification level, a magnification level chosen by the user via the at least one operating element and the assignment stored in the control unit to generate appropriate control signals and to transmit the appropriate control signals to the actuator.

15. The device as claimed in claim 14, wherein the control unit is furthermore configured to record a magnification change or the end position reached for the user via optical, acoustic or other signaling perceptible to the user.

16. The device as claimed in claim 1, wherein the control unit is furthermore configured to record a magnification change or an end position reached for the user via optical, acoustic or other signaling perceptible to the user.

17. The device as claimed in claim 1, wherein the control unit is furthermore configured to show the currently selected magnification level via an imaging unit.

18. The device as claimed in claim 1, further comprising at least one optical element which can be inserted in a free passage of the incremental magnification changer only in one direction and not in the opposite direction.

19. The device as claimed in claim 18, wherein the at least one optical element which is insertable into the free passage of the magnification changer is a further Galilean telescope.

20. The device as claimed in claim 18, wherein the at least one optical element which is insertable into the free passage of the incremental magnification changer is automatically inserted upon the free passage being activated in a predetermined direction.

21. A device for actuator-driven adjustment of incremental magnification levels of a magnification changer, comprising:

at least one sensor coupled to the magnification changer that detects and transmits a currently selected incremental magnification level to a control unit;

the control unit further including a stored assignment of the incremental magnification levels present on the magnification changer in a sequence of the incremental magnification levels ordered according to numerical size;

at least one operating element that enables choosing a desired magnification level, wherein the at least one operating element that enables choosing the desired magnification level is presented to a user and is connected to the control unit; and wherein the magnification changer that sets the magnification level chosen by the user via the at least one operating element further comprises an actuator which is connected to and controlled by the control unit and which receives corresponding control signals from the control unit and that is operably coupled to the magnification changer to change the magnification level thereof, and wherein the magnification changer is based on Galilean telescopes.

22. The device as claimed in claim 21, wherein the magnification changer has one free passage without lenses and two passages each with a Galilean telescope, which passages are arranged offset by approximately 60° and are brought into a beam path by a rotational movement.

23. The device as claimed in claim 21, wherein the magnification changer has passages including one free passage without lenses and at least one passage with a Galilean telescope, which passages are arranged evenly distributed and are brought into a beam path by a rotational movement.

\* \* \* \* \*

UNITED STATES PATENT AND TRADEMARK OFFICE
CERTIFICATE OF CORRECTION

PATENT NO. : 11,953,667 B2
APPLICATION NO. : 16/638571
DATED : April 9, 2024
INVENTOR(S) : Golz et al.

It is certified that error appears in the above-identified patent and that said Letters Patent is hereby corrected as shown below:

In the Specification

Column 2, Line 26, delete "11 000" and insert --11,000--

Column 3, Line 5, delete "3633" and insert --3633.--

Column 3, Line 8, delete "1721" and insert --1721.00--

In the Claims

Column 8, Line 57, delete "thereof, and" and insert --thereof; and--

Signed and Sealed this
Twenty-third Day of July, 2024

*Katherine Kelly Vidal*

Katherine Kelly Vidal
*Director of the United States Patent and Trademark Office*